US011813062B2

(12) United States Patent
Govari et al.

(10) Patent No.: US 11,813,062 B2
(45) Date of Patent: Nov. 14, 2023

(54) SOLVING DOUBLE POTENTIAL PROBLEMS

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 140 days.

(21) Appl. No.: 16/718,427

(22) Filed: Dec. 18, 2019

(65) Prior Publication Data

US 2021/0186348 A1 Jun. 24, 2021

(51) Int. Cl.
*A61B 5/25* (2021.01)
*A61B 5/325* (2021.01)
*A61B 5/339* (2021.01)
*A61B 5/00* (2006.01)

(52) U.S. Cl.
CPC ............... *A61B 5/25* (2021.01); *A61B 5/325* (2021.01); *A61B 5/339* (2021.01); *A61B 5/72* (2013.01); *A61B 5/742* (2013.01)

(58) Field of Classification Search
CPC .......... A61B 5/25; A61B 5/325; A61B 5/339; A61B 5/72; A61B 5/742; A61B 5/7221; A61B 5/7239; A61B 5/065; A61B 5/6852; A61B 5/353; A61B 5/367; A61B 5/0044; A61B 2505/05
See application file for complete search history.

(56) References Cited

U.S. PATENT DOCUMENTS

| 6,236,883 | B1 | 5/2001 | Ciaccio |
| 6,690,963 | B2 | 2/2004 | Ben Haim |
| 10,314,542 | B2 | 6/2019 | Bar-Tal |
| 10,335,052 | B2 | 7/2019 | El Haddad |

(Continued)

OTHER PUBLICATIONS

European Search Report for corresponding EPA No. 20215145.2 dated May 7, 2021.

(Continued)

*Primary Examiner* — Mallika D Fairchild
*Assistant Examiner* — Shreya Anjaria
(74) *Attorney, Agent, or Firm* — Dergosits & Noah LLP; Todd A. Noah (57) ABSTRACT

A method for electrophysiological assessment, including acquiring electrical signals from locations of a region of ablated tissue in a heart chamber, and deriving from the signals respective annotations, which are indicative of times within a heart cycle at which a conduction wave traversed the locations. The method includes identifying a first location, at a first distance from the region, where the electrical signals include a double-potential signal, having first and second annotations at different times within the heart cycle, and identifying, in proximity to the first location, a second location, at a second distance from the region, greater than the first distance, where the electrical signals have a third annotation. The method further includes selecting one of the first and second annotations that is closest to the third annotation as a valid annotation for the first location, and displaying the valid annotation on an electroanatomical map of the heart.

17 Claims, 6 Drawing Sheets

(56) References Cited

U.S. PATENT DOCUMENTS

| | | | |
|---|---|---|---|
| 2012/0184863 A1* | 7/2012 | Harlev | A61B 5/349 |
| | | | 600/509 |
| 2017/0079539 A1 | 3/2017 | Chauhan | |
| 2017/0172508 A1 | 6/2017 | Hultz | |
| 2018/0235495 A1 | 8/2018 | Rubenstein | |
| 2018/0296108 A1* | 10/2018 | Stewart | A61B 5/349 |
| 2018/0296167 A1* | 10/2018 | Stewart | A61B 5/7267 |
| 2019/0336022 A1* | 11/2019 | Harlev | A61B 5/7221 |

OTHER PUBLICATIONS

Raymond W. Sy, "Modern Electrophysiology Mapping Techniques", Heart, Lung and Circulation 2012; 21: 364-375.

* cited by examiner

SOLVING DOUBLE POTENTIAL PROBLEMS

FIELD OF THE INVENTION

The present invention relates generally to invasive medical procedures, and specifically to analyzing results of a cardiac invasive procedure.

BACKGROUND OF THE INVENTION

An invasive cardiac procedure typically includes acquiring intra-cardiac (IC) electrocardiograph (ECG) signals, and analyzing the signals. Analysis of IC ECG signals is well known in the art.

For example, U.S. Pat. No. 10,314,542 to Bar-Tal et al. describes a system for determining regions of interest for heart ablation using fractionation. The method can comprise detecting, via sensors, electro-cardiogram (ECG) signals, each ECG signal detected via one of the sensors and indicating electrical activity of a heart. The system also includes determining regions of interest for heart ablation in accordance with the fractionation.

U.S. Patent Application No. 2018/0235495 to Rubenstein describes cardiac mapping catheters and methods for using the catheters. A catheter can detect the presence, direction and/or source of a depolarization wave front associated with cardiac arrhythmia.

U.S. Pat. No. 10,335,052 to El Haddad describes a device for analyzing electrophysiological data. The device generates a signal indicative for a presence of a pulmonary vein potential component using processing means adapted for performing a stepwise analysis of the electrophysiological data.

U.S. Pat. No. 6,236,883 to Ciaccio et al. describes a method comprising the steps of identifying and localizing reentrant circuits from electrogram features using feature detection and localization (FDL) algorithms.

U.S. Patent Application No. 2017/0079539 to Chauhan et al. describes a system for identifying focal source locations of electrophysiological activity in an organ. The system may also be used to guide catheter ablation of the organ.

SUMMARY OF THE INVENTION

An exemplary embodiment of the present invention provides a method for electrophysiological assessment, including:

acquiring electrical signals from myocardial tissue at multiple locations in a vicinity of a region of ablated tissue in a chamber of a heart;

deriving from the electrical signals respective annotations, which are indicative of times within a cycle of the heart at which a conduction wave in the myocardial tissue traversed the locations;

identifying a first location, at a first distance from the region of the ablated tissue, where the electrical signals include a double-potential signal, having a first annotation and a second annotation at different, respective times within the cycle of the heart;

identifying, in proximity to the first location, a second location, at a second distance from the region of the ablated tissue, greater than the first distance, where the electrical signals have a third annotation;

selecting one of the first annotation and the second annotation that is closest to the third annotation as a valid annotation for the first location; and displaying the valid annotation on an electroanatomical map of the heart.

In a disclosed exemplary embodiment the electrical signals at the second location include a single-potential signal or a double-potential signal.

In another disclosed exemplary embodiment the chamber includes an atrium of the heart.

In yet another disclosed exemplary embodiment the chamber includes a ventricle of the heart.

In a further disclosed exemplary embodiment the region of the ablated tissue includes one or more separated points. Alternatively or additionally the region of the ablated tissue includes a line segment.

In an alternative exemplary embodiment displaying the valid annotation on the electroanatomical map includes deriving a local activation time (LAT) for the first location from the valid annotation, and incorporating the LAT into the map.

In a further alternative exemplary embodiment the first location is within a preset threshold distance from the region of ablated tissue. The preset threshold distance may be 10 mm.

There is further provided, according to an exemplary embodiment of the present invention, apparatus for electrophysiological assessment, including: a display, configured to present an electroanatomical map of a heart;

a probe, configured to acquire electrical signals from myocardial tissue at multiple locations in a vicinity of a region of ablated tissue in a chamber of the heart; and a processor, configured to:

derive from the electrical signals respective annotations, which are indicative of times within a cycle of the heart at which a conduction wave in the myocardial tissue traversed the locations, identify a first location, at a first distance from the region of the ablated tissue, where the electrical signals include a double-potential signal, having a first annotation and a second annotation at different, respective times within the cycle of the heart, identify, in proximity to the first location, a second location, at a second distance from the region of the ablated tissue, greater than the first distance, where the electrical signals have a third annotation, select one of the first annotation and the second annotation that is closest to the third annotation as a valid annotation for the first location, and display the valid annotation on the electroanatomical map of the heart.

BRIEF DESCRIPTION OF THE DRAWINGS

The present invention will be more fully understood from the following detailed description of the exemplary embodiments thereof, taken together with the drawings, in which.

DETAILED DESCRIPTION OF EMBODIMENTS

Overview

If a section of heart tissue has been ablated, typically along an ablation line, there is a high probability of the occurrence of double potentials in locations near the ablation, i.e., instead of there being a signal with one annotation, the signal has two annotations. Only one of the annotations is representative of the time at which a conduction wave traverses a given location but a system processor may choose the wrong one.

In exemplary embodiments of the present invention the system processor is aware of the location of ablation regions. For points close to an ablation region, and where double potentials occur, the processor uses this awareness to choose which of the double potential annotations is assumed to be the correct one. The chosen annotation is the one closer in time to the annotations of neighboring points that are farther from the ablation region.

Thus, in an exemplary embodiment of the present invention electrical signals are acquired from myocardial tissue at multiple locations in a vicinity of a region of ablated tissue in a chamber of a heart. From the electrical signals respective annotations, which are indicative of times within a cycle of the heart at which a conduction wave in the myocardial tissue traversed the locations, are derived.

A first location that is at a first distance from the region of the ablated tissue is identified, the first location being where the electrical signals comprise a double-potential signal, having a first annotation and a second annotation at different, respective times within the cycle of the heart.

A second location, that is in proximity to the first location, and that is at a second distance, greater than the first distance, from the region of the ablated tissue, is identified. The second location has electrical signals that have a third annotation.

The one of the first annotation and the second annotation that is closest to the third annotation is selected as a valid annotation for the first location. The valid annotation is then displayed on an electroanatomical map of the heart.

System Description

In the following description, like elements in the drawings are identified by like numerals, and like elements are differentiated as necessary by appending a letter to the identifying numeral.

Figure 1:
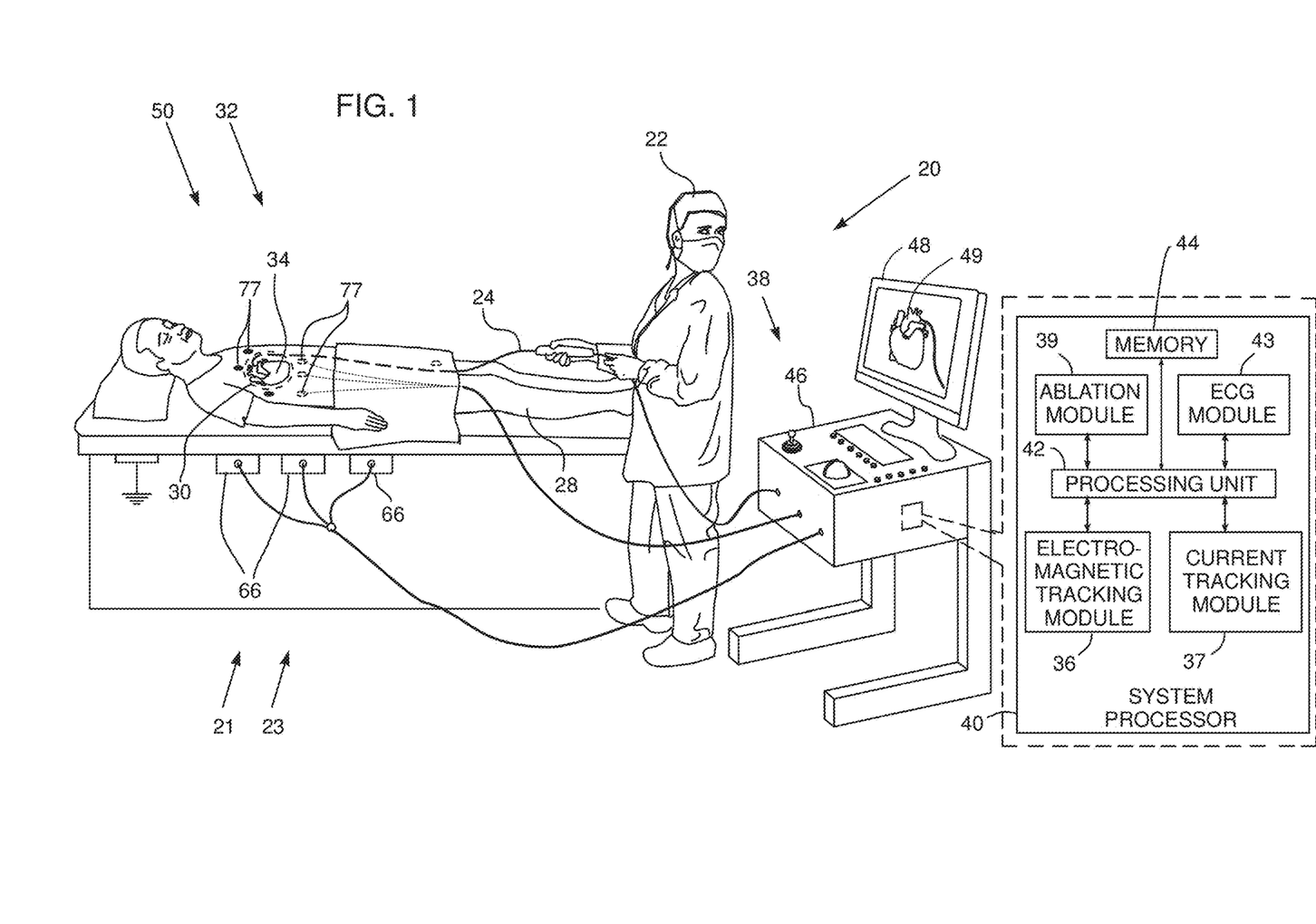
FIG. 1 is a schematic illustration of a double potential analysis system, according to an exemplary embodiment of the present invention.
Figure 2:
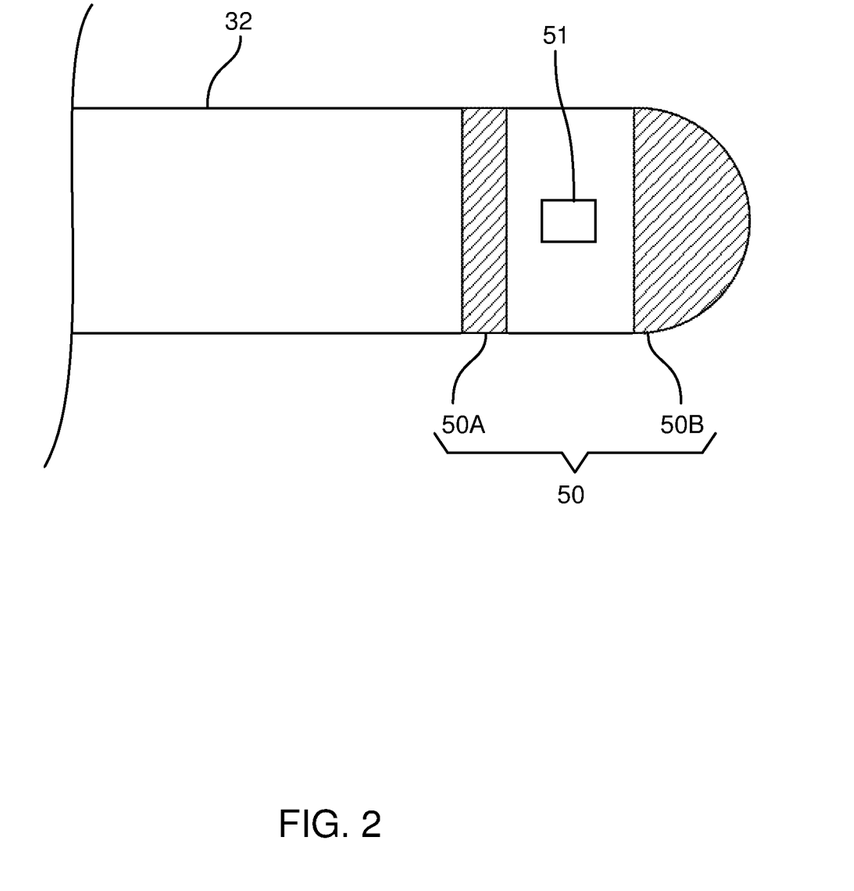
FIG. 2 is a schematic illustration of a distal end of a catheter used in the system, according to an exemplary embodiment of the present invention.

Reference is now made to FIG. 1, which is a schematic illustration of a double potential analysis system 20, and to FIG. 2, which is a schematic illustration of a distal end of a catheter used in the system, according to an embodiment of the present invention. For simplicity and clarity, the following description, except where otherwise stated, assumes a medical procedure is performed by an operator 22 of system 20, herein assumed to be a medical practitioner, wherein the operator inserts a catheter 24 into a left or right femoral vein of a patient 28. The procedure is assumed to comprise investigation of a chamber of a heart 34 of the patient, and in the procedure, the catheter is initially inserted into the patient until a distal end 32 of the catheter, also herein termed probe 32, reaches the heart chamber. The chamber typically comprises an atrium or a ventricle of the heart.

System 20 may be controlled by a system processor 40, comprising a processing unit (PU) 42 communicating with an electromagnetic tracking module 36 and/or a current tracking module 37. PU 42 also communicates with an ablation module 39 and an ECG (electrocardiograph) module 43. The functions of the modules are described in more detail below. PU 42 also communicates with a memory 44. Processor 40 is typically mounted in a console 46, which comprises operating controls 38, typically including a pointing device such as a mouse or trackball, that operator 22 uses to interact with the processor. The processor uses software stored in memory 44 to operate system 20. Results of the operations performed by processor 40 are presented to the operator on a display 48. The results, which are typically in the form of an electroanatomical map 49 of heart 34, enable the operator to form an electrophysiological assessment of the heart. The software may be downloaded to processor 40 in electronic form, over a network, for example, or it may, alternatively or additionally, be provided and/or stored on non-transitory tangible media, such as magnetic, optical, or electronic memory.

For tracking the path of probe 32 in a mapping region containing heart 34, exemplary embodiments of the present invention use at least one of a current based tracking system 21 and an electromagnetic based tracking system 23. Both systems are described below.

Tracking system 21 comprises a current measuring tracking system, similar to that described in U.S. Pat. No. 8,456,182 to Bar-Tal et al., whose disclosure is incorporated herein by reference. The Carto® system produced by Biosense-Webster of 33 Technology Drive, Irvine, Calif. 92618 USA, also uses a current measuring tracking system. The current measuring tracking system is under control of current tracking module 37. Probe 32 has one or more probe electrodes 50, herein by way of example assumed to comprise an electrode 50A and an electrode 50B, and in tracking system 21 module 37 injects currents to the one or more electrodes 50 being tracked. The currents are received, by a plurality of generally similar patch electrodes 77, also herein termed patches, which are positioned on the skin of patient 28, and transferred back to the module.

While conductive cabling to patch electrodes 77 and for other skin electrodes described herein is present for each of the electrodes, for clarity cabling is only shown in the figure for some of the electrodes. The currents between a given probe electrode 50 and skin patches 77 vary according to the location of the electrode, because, inter alia, of the different distances of the electrode from the patches, which cause different impedances between the given probe electrode and the different patches. Module 37 measures the different currents received by the different patches 77 on respective channels connected to the patches, and may be configured to generate an indication of the location of the given probe electrode from the different currents.

Electromagnetic tracking system 23 is similar to that described in U.S. Pat. No. 6,690,963 to Ben-Haim et al., whose disclosure is incorporated herein by reference, and to that used in the Carto™ system produced by Biosense-Webster. The electromagnetic tracking system is under control of electromagnetic tracking module 36. The electromagnetic tracking system comprises a plurality of magnetic field generators, herein assumed to comprise three sets of generators 66, each set comprising three orthogonal coils, so that the plurality of generators comprises a total of nine coils. Generators 66 are placed in known locations beneath patient 28, the known locations defining a frame of reference of the generators. Module 36 controls, inter alia, the amplitude and frequency of the alternating magnetic fields produced by the generators.

The alternating magnetic fields interact with a coil 51 located in probe 32, so as to generate alternating electropotentials in the coil, and the electropotentials are received as a signal by tracking module 36. The module, together with processing unit 42, analyzes the received signal, and from the analysis is able to determine a position, i.e., a location and an orientation, of the probe coil in the defined frame of reference.

Typically the tracking by either or both of the systems may be presented visually on display 48, for example by incorporating an icon representing the probe into map 49 of heart 34, as well as a path taken by the icon. For clarity, in the following description, only electromagnetic tracking system 23 is assumed to be use, but the description may be adapted, mutatis mutandis, for cases where both system 23 and system 21 are used, or if only system 21 is used.

Ablation module 39 comprises a radiofrequency (RF) generator which delivers RF power to a region of heart 34 that is selected by operator 22, so as to ablate the region. Operator 22 selects the region by positioning an ablation probe, with an ablation electrode, at the region. In some embodiments probe 32 and one of electrodes 50, such as electrode 50B, may be used as an ablation probe and an ablation electrode. Alternatively a separate ablation probe and ablation electrode may be used for the ablation provided by module 39.

ECG module 43 receives intra-cardiac (IC) ECG signals acquired by electrodes 50 when the electrodes are in contact with myocardial tissue of a chamber of heart 34. The ECG module together with PU 42 analyzes the signals, as described below, to find, inter alia, local activation times (LATs) of the signals. The module typically formulates its measurements relative to a reference ECG signal, such as may be provided by an electrode positioned in the coronary sinus of heart 34.

Figure 3:
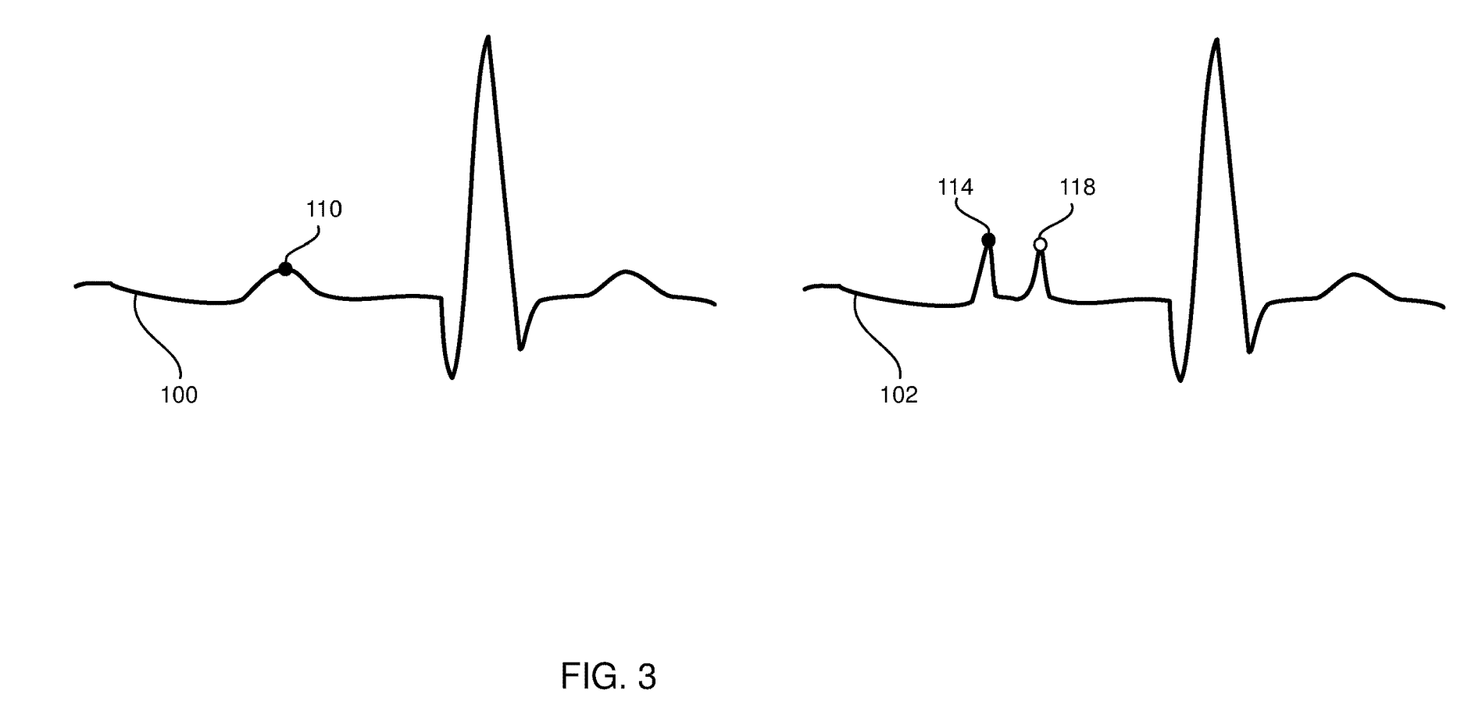
FIG. 3 shows examples of intra-cardiac electrocardiograph signals, according to an exemplary embodiment of the present invention.

FIG. 3 shows examples of IC ECG signals, according to an embodiment of the present invention. Signals 100 and 102 are acquired by electrodes 50 in contact with respective locations of the myocardial tissue of the heart chamber, herein by way of example assumed to be an atrium. The signals are voltage versus time signals, and for simplicity axes for the signals are not illustrated in FIG. 3. PU 42 and module 43 analyze each signal to determine one or more annotations of each of the signals. An annotation for a given location is indicative of a time, the LAT, in the cycle of the beating heart at which a conduction wave in the heart traverses the location, and is assumed herein to comprise an ordered pair of the signal, i.e., a voltage V and a time t of the signal.

As is known in the art, the annotation for a given ECG signal may be set by different methods. For example, the annotation for a ventricle may be selected to be at a point on the QRS complex wherein the negative slope is steepest, i.e., wherein $$\frac{dV}{dt}$$

is most negative. For an atrium the annotation may be set at the maximum of the P-wave of the signal, or alternatively at the time where $$\frac{dV}{dt}$$

of the P-wave is most negative.

In the following description, except where otherwise stated, IC ECG signals are assumed to be acquired from an atrium of the heart, and the annotation for the acquired signals is assumed to be at the time of the maximum of the P-wave signal. Cases where the annotation of the P-wave is at other positions, such as at the time where $$\frac{dV}{dt}$$

is most negative, are noted further below.

Signal 100 illustrates a signal having a single annotation 110, at the peak of the P-wave, and such signals are also termed single potential signals. Signals having a single annotation, such as signal 100, are typically generated by heart 34 when it is beating in sinus rhythm.

Signal 102 illustrates a signal having two annotations 114, 118, wherein the P-wave has two peaks, and such signals are termed double-potential signals. While a heart beating in sinus rhythm may generate double-potential signals, the presence of double potentials may be indicative of, for example, an arrhythmia, scar tissue, or ablated tissue.

As explained below, signals such as those illustrated in FIG. 3 are used to produce electroanatomical map 49 of heart 34.

Figure 4A:
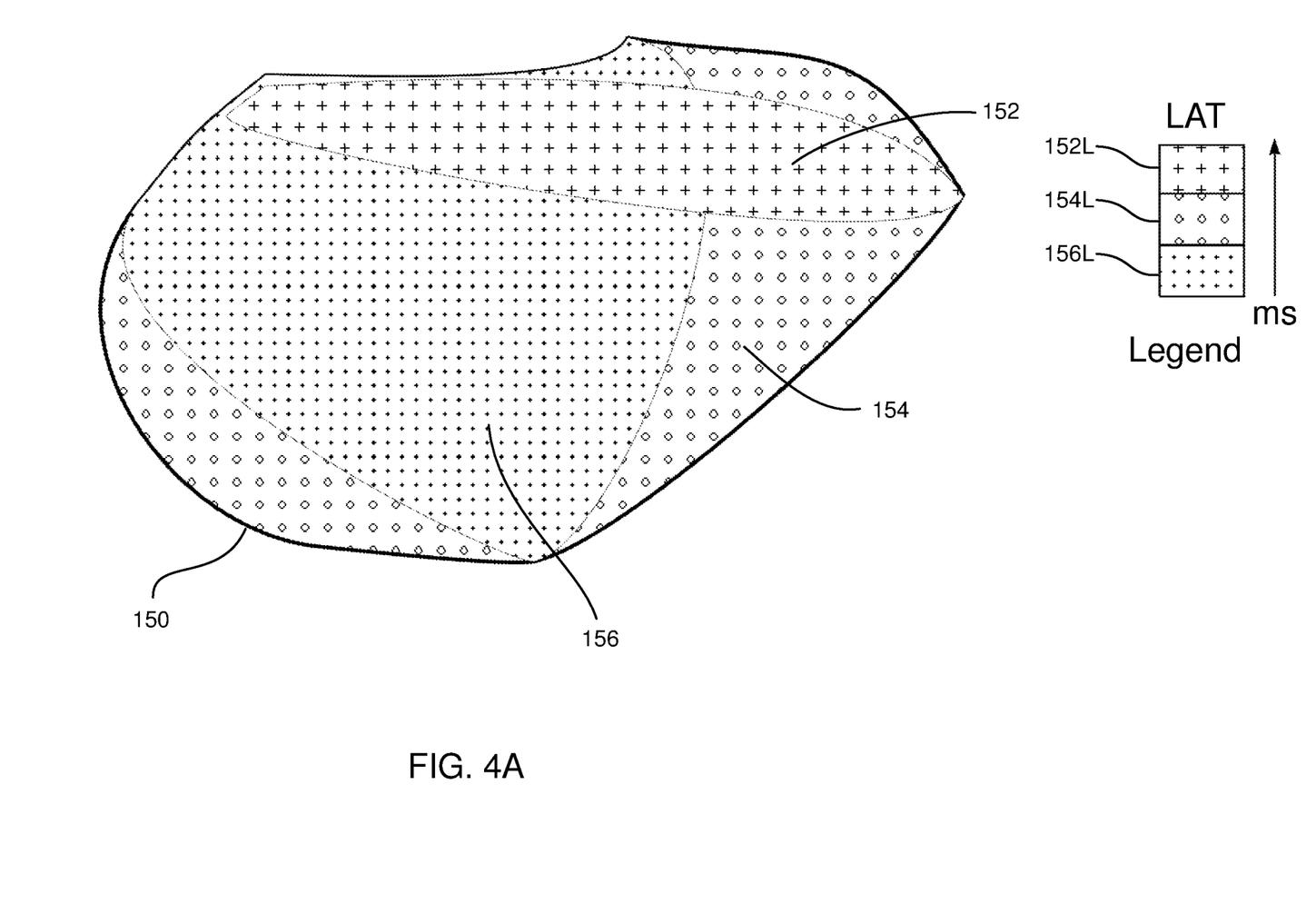
FIG. 4A is a schematic illustration of an electroanatomical map of a section of heart chamber tissue, according to an exemplary embodiment of the present invention.

FIG. 4A is a schematic illustration of an electroanatomical map 150 of a section of an atrium of heart 34, according to an embodiment of the present invention. Map 150 is produced before ablation of myocardial tissue of heart 34 and the map illustrates a portion of electroanatomical map 49.

To produce map 49, a three-dimensional (3D) map of the heart chamber may be first generated, by moving distal end 32 within the heart chamber, and tracking and recording positions of the distal end using one of the tracking systems referred to above. The recorded positions comprise a point cloud of positions within and at a surface of the heart chamber, and processor 40 may then analyze the point cloud, by methods which are well known in the art, to produce a 3D envelope enclosing the point cloud, the envelope corresponding to the tissue surface of the atrium.

Once the 3D map has been produced, the surface of the atrium may be characterized by acquiring and recording IC ECG signals from locations on the surface of the atrium. The signal acquisition may be performed using electrodes 50 of distal end 32, while recording the location of the distal end, and thus of the electrodes. The characterization may be as illustrated above for the signals of FIG. 3, comprising processor 40 calculating annotations for the signals. From the annotations the processor may initially assign LATs to the locations where the IC ECG signals are acquired, by methods which are well known in the art.

For single potential signals the LAT typically corresponds to the time of the single potential annotation, i.e., the time of the P-wave maximum. Thus, for signal 100, the LAT is at the time of annotation 110. For double potential signals the LAT, except as described further below, is assumed to correspond to the time of the annotation having the largest voltage. (If the annotation is defined in terms of the $$\frac{dV}{dt}$$

of the signal, the LAT may be assumed to correspond to the time of the annotation having the most negative $$\frac{dV}{dt}.\}$$

Thus, for signal 102, if annotation 114 has a larger voltage than annotation 118, the LAT is at the time of annotation 114. In displays of the annotated signals, referred to further below, typically only the annotation selected for the LAT is superimposed on signals. In FIG. 3 annotation 114 has been drawn as a filled circle to indicate it is the annotation that has been selected for the LAT of signal 102. Similarly, annotation 110 has been drawn as a filled circle to indicate it is the annotation that has been selected for the LAT of signal 100.

Once the LAT values for specific locations have been determined, the processor may overlay the measured values on the 3D map of the chamber, typically interpolating between the values, to produce an electroanatomical map. The different LAT values are typically illustrated in maps 150 and 49 as different colors, but are shown schematically for regions 152, 154, 156 of the atrium in FIG. 4A as respective different types of shading 152L, 154L, 156L. The values, typically in ms, of the LATs may be shown on display 48 as a legend for the map, as is schematically illustrated in FIG. 4A.

Operator 22 may assess map 150, and from the assessment may decide to ablate a region of the myocardial tissue, typically to correct a problem such as arrhythmia that is occurring in heart 34. To perform the ablation, the operator moves distal end 32 so that electrodes 50 are at a selected location of the tissue. The movement is tracked by one of the tracking systems referred to above, and the selected location, when reached, may be recorded by processor 40.

In addition to recording the selected location, once the operator has performed ablation at the location, the location may be marked on map 49, as described below with reference to FIG. 4B.

Figure 4B:
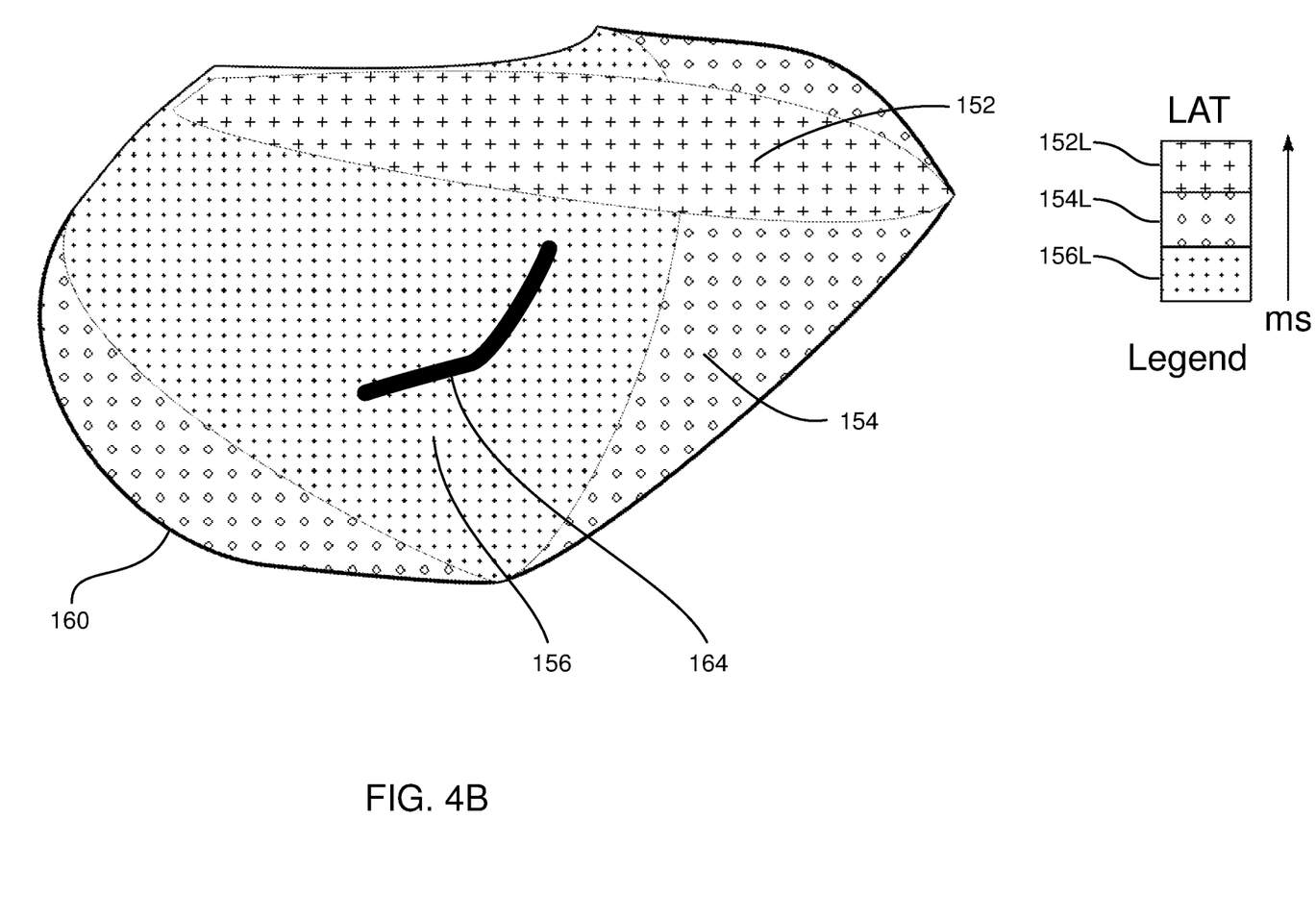
FIG. 4B is a schematic illustration of a map of a section of heart chamber tissue, after ablation has been performed, according to an exemplary embodiment of the present invention.

FIG. 4B is a schematic illustration of a map 160 of a section of the atrium of heart 34, after ablation has been performed, according to an embodiment of the present invention. Except as described below, map 160 is substantially similar to map 150, so that the positions of regions 152, 154, and 156 are the same in the two maps. Map 160 also comprises a marked location 164 on the atrium indicating where ablation has been performed. By way of example, the ablation is assumed to have been on a line, but it will be appreciated that substantially any type of figure, including point regions, may be marked on the map of the atrium in a similar manner to location 164.

After the ablation illustrated in map 160, operator 22 may re-acquire IC ECG signals from the tissue, to assess the efficacy of the ablation and to update the map. The flowchart of FIG. 5, below, illustrates steps of an algorithm performed by processor 40 when the operator re-acquires the signals.

Figure 5:
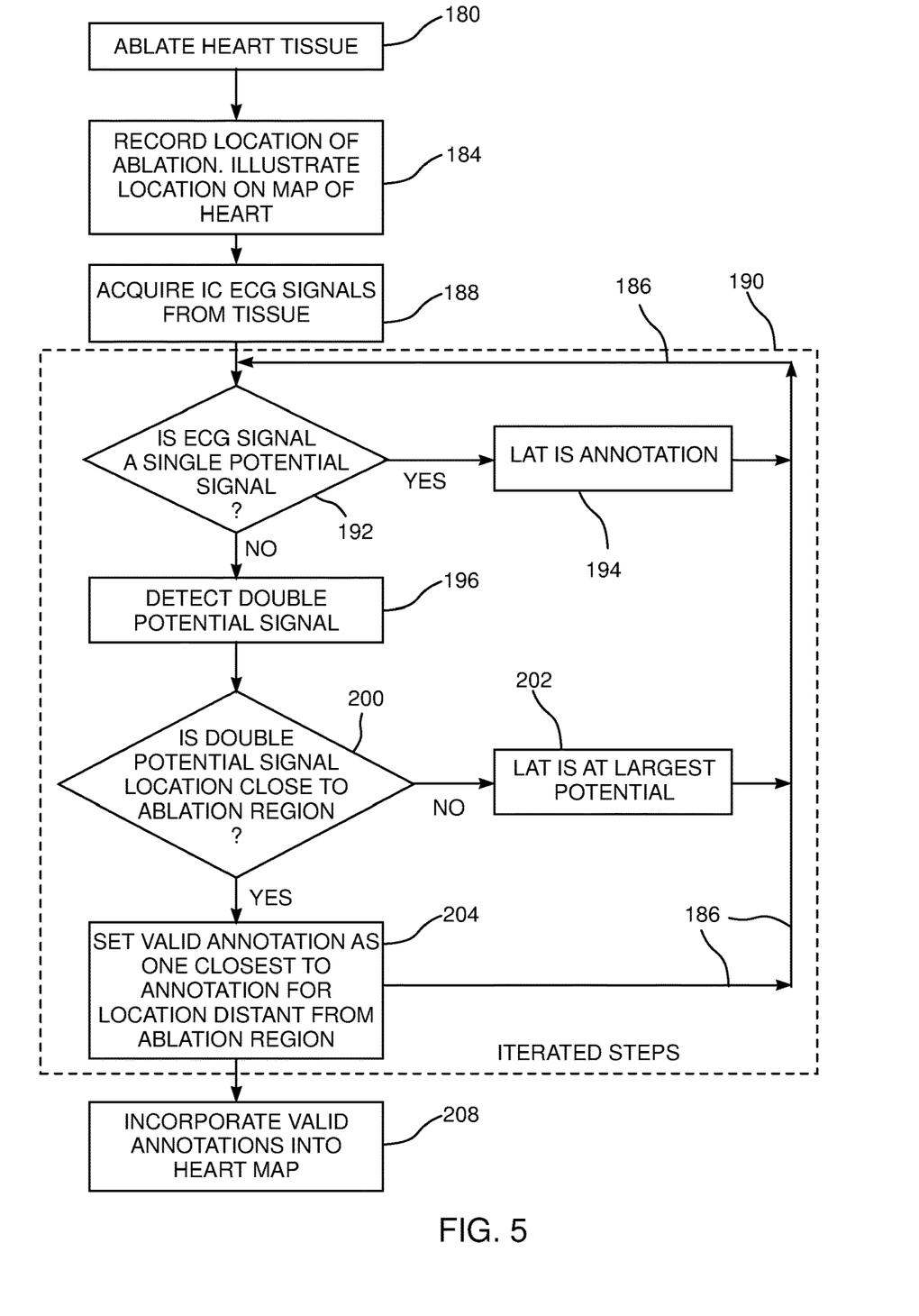
FIG. 5 is a flowchart of steps of an algorithm performed by a processor of the system, according to an exemplary embodiment of the present invention.

FIG. 5 is a flowchart of steps of an algorithm performed by processor 40, according to an embodiment of the present invention. In an initial step 180 operator 22 assesses an electroanatomical map of an atrium of heart 34, herein assumed to correspond to map 49, and as a result of the assessment the operator decides to ablate a region of the myocardial tissue of the atrium. The ablated region may comprise one or more separated points of the tissue; alternatively, the ablated region may be in the form of a line segment, similar to that illustrated in map 160 of FIG. 4B.

In a record step 184, processor 40 records the locations of the ablation performed, and also illustrates the locations on map 49 displayed to the operator. The illustration typically comprises incorporating one or more icons into map 49.

In a signal acquisition step 188, the operator moves probe 32 to locations on the surface of the atrium, and electrode 50 acquires respective ECG signals at each of the locations. Processor 40, together with module 43, stores the signals. For each acquired ECG signal the processor analyzes the signal to determine one or more annotations in the signal. The processor stores the annotations and the locations at which the signals providing the annotations were acquired.

Except where stated otherwise, processor 40 iterates the following steps of the flowchart, as is shown by arrows 186, in order to analyze the acquired results. The iterated steps of the flowchart are shown in FIG. 5 as enclosed in a dashed line rectangle 190. In the iteration, the processor separately analyzes each of the acquired ECG signals, and their stored annotations and locations as described above.

In a first decision step 192, processor 40 checks if the signal is a single potential signal, i.e., if the signal has a single annotation. If decision 192 returns positive, in an assignation step 194 the processor assigns the time of the annotation to be the LAT of the location. If decision 192 returns negative, the flowchart continues to a double potential step 196.

In step 196 processor 40 determines that the analyzed signal is a double potential signal.

In a second decision step 200, processor 40 calculates the respective distances of the location of the signal from the ablated regions, and assesses if the location is close to the regions. I.e., the processor calculates the distances of the location of the signal from all of the ablated regions, and determines if any of the distances are within a preset threshold distance. In one embodiment the threshold distance is set to be 10 mm.

If step 200 returns negative, i.e., the signal location is not within the preset threshold distance, so is far from the ablated regions, in a further assessment step 202 the processor assumes the LAT for the location of the double potential corresponds to the annotation with the largest potential.

If step 200 returns positive, i.e., the signal location is within the preset threshold distance, then the location is close to at least one of the ablated regions. In this case, in an annotation allocation step 204 the processor assumes that the LAT for the location, the valid annotation, is the annotation that is closest to an annotation for a neighboring location that is farther from the ablated region. It will be understood that the signal of the neighboring location may be a single potential signal or a double potential signal.

Once processor 40 has completed analysis of all the ECG signals acquired in step 188, i.e., the processor has completed the iterative steps described above, the processor updates map 49 in an update step 208. In the update step the processor incorporates the valid annotations of steps 194, 202, and 204 into map 49, by displaying LAT values of the annotations in the map. By inspection of the updated map, operator 22 is able to use results generated as described above to assess the efficacy of the ablation performed in initial step 180.

The description above assumes that the annotation of the P-wave is at the time of the maximum of the P-wave. The description may be changed, mutatis mutandis, to accommodate cases where the annotation of the P-wave is at other positions known in the art, such as at the time of the most negative $$\frac{dV}{dt}$$

of the P-wave.

For clarity, the description above assumes that double-potential signals are acquired from an atrium of a heart, and are analyzed according to the algorithm of FIG. 5. The description above, mutatis mutandis, also applies to double-potential signals generated in a ventricle of the heart. Thus, embodiments of the present invention comprise analysis of double-potential signals generated in any chamber of the heart.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for electrophysiological assessment, comprising:
   causing a selected region of tissue in a chamber of a heart to be ablated by a probe;
   receiving, by a processor of a computing system, electrical signals acquired by the probe from myocardial tissue at multiple locations in a vicinity of the region of ablated tissue and storing, by the processor, the acquired electrical signals in a memory of the computing system;
   determining, by the processor, for each acquired electrical signal, whether the electrical signal comprises a single-potential signal having a single annotation or a double-potential signal having a first annotation and a second annotation at different, respective times within the cycle of the heart;
   storing, by the processor, in the memory of the computing system, the annotations of the acquired signals and the locations at which the signals providing the annotations were acquired;
   assigning, by the processor, for each determined single-potential signal, a local activation time (LAT) corresponding to the single annotation;
   determining, by the processor, for each determined double-potential signal, a distance of the signal from the region of the ablated tissue and whether the distance is within a preset threshold;
   assigning, by the processor, for each determined double-potential signal having a distance not within the preset threshold, the LAT corresponding to the first annotation or the second annotation of the double-potential signal with a larger potential;
   assigning, by the processor, for each determined double-potential signal having a distance within the preset threshold, the LAT corresponding to the first annotation or the second annotation of the double-potential signal that is closest to an annotation for a neighboring signal having a distance from the region of the ablated tissue greater than the first or second annotation; and
   causing, by the processor, each of the assigned LATs to be displayed on a three-dimensional electroanatomical map of the heart.

2. The method according to claim 1, wherein the chamber comprises an atrium of the heart.

3. The method according to claim 1, wherein the chamber comprises a ventricle of the heart.

4. The method according to claim 1, wherein the region of the ablated tissue comprises one or more separated points.

5. The method according to claim 1, wherein the region of the ablated tissue comprises a line segment.

6. The method according to claim 1, wherein the predetermined distance is 10 mm.

7. Apparatus for electrophysiological assessment, comprising:
   one or more processors of a computing system; and
   a non-transitory computer readable medium storing a plurality of instructions, which when executed, cause the one or more processors to:
   cause a selected region of tissue in a chamber of a heart to be ablated by a probe;
   receive electrical signals acquired by the probe from myocardial tissue at multiple locations in a vicinity of the region of ablated tissue and store the acquired electrical signals in a memory of the computing system;
   derive from the electrical signals respective annotations, which are indicative of times within a cycle of the heart at which a conduction wave in the myocardial tissue traversed the locations,
   determine, for each acquired electrical signal, whether the electrical signal comprises a single-potential signal having a single annotation or a double-potential signal having a first annotation and a second annotation at different, respective times within the cycle of the heart;
   store, in the memory of the computing system, the annotations of the acquired signals and the locations at which the signals providing the annotations were acquired;
   assign, for each determined single-potential signal, a local activation time (LAT) corresponding to the single annotation;
   determine, for each determined double-potential signal, a distance of the signal from the region of the ablated tissue and whether the distance is within a preset threshold;
   assign, for each determined double-potential signal having a distance not within the preset threshold, the LAT corresponding to the first annotation or the second annotation of the double-potential signal with a larger potential;
   assign, for each determined double-potential signal having a distance within the preset threshold, the LAT corresponding to the first annotation or the second annotation of the double-potential signal that is closest to an annotation for a neighboring signal with a distance from the region of the ablated tissue greater than the first or second annotation; and
   cause each of the assigned LATs to be displayed a three-dimensional electroanatomical map of the heart.

8. The apparatus according to claim 7, wherein the chamber comprises an atrium of the heart.

9. The apparatus according to claim 7, wherein the chamber comprises a ventricle of the heart.

10. The apparatus according to claim 7, wherein the region of the ablated tissue comprises one or more separated points.

11. The apparatus according to claim 7, wherein the region of the ablated tissue comprises a line segment.

12. The apparatus according to claim 7, wherein the predetermined distance is 10 mm.

13. A computer program product, comprising a non-transitory computer-readable medium having computer-readable program code embodied therein to be executed by one or more processors of a computing system, the program code including instructions to:
cause a selected region of tissue in a chamber of a heart to be ablated by a probe;
receive, by the one or more processors, electrical signals acquired by the probe from myocardial tissue at multiple locations in a vicinity of the region of ablated tissue and storing, by the one or more processors, the acquired electrical signals in a memory of the computing system;
determine, by the one or more processors, for each acquired electrical signal, whether the electrical signal comprises a single-potential signal having a single annotation or a double-potential signal having a first annotation and a second annotation at different, respective times within the cycle of the heart;
store, by the one or more processors, in the memory of the computing system, the annotations of the acquired signals and the locations at which the signals providing the annotations were acquired;
assign, by the one or more processors, for each determined single-potential signal, a local activation time (LAT) corresponding to the single annotation;
determine, by the one or more processors, for each determined double-potential signal, a distance of the signal from the region of the ablated tissue and whether the distance is within a preset threshold;
assign, by the one or more processors, for each determined double-potential signal having a distance not within the preset threshold, the LAT corresponding to the first annotation or the second annotation of the double-potential signal with a larger potential;
assign, by the one or more processors, for each determined double-potential signal having assign, by the one or more processors, for each determined double-potential signal having a distance within the preset threshold, the LAT corresponding to the first annotation or the second annotation of the double-potential signal that is closest to an annotation for a neighboring signal having a distance from the region of the ablated tissue greater than the first or second annotation; and
cause, by the one or more processors, each of the assigned LATs to be displayed on a three-dimensional electro-anatomical map of the heart.

14. The computer program product according to claim 13, wherein the chamber comprises an atrium of the heart.

15. The computer program product according to claim 13, wherein the chamber comprises a ventricle of the heart.

16. The computer program product according to claim 13, wherein the region of the ablated tissue comprises one or more separated points.

17. The computer program product according to claim 13, wherein the region of the ablated tissue comprises a line segment.

* * * * *